United States Patent [19]

Prager et al.

[11] Patent Number: 5,182,383
[45] Date of Patent: Jan. 26, 1993

[54] STABLE, CRYSTALLINE FORM OF A CEPHALOSPORIN INTERMEDIATE PRODUCT

[75] Inventors: Bernhard C. Prager, Wörgl; Karl Wessely; Werner Veit, both of Kufstein, all of Austria

[73] Assignee: Biochemie Gesellschaft m.b.H., Tyrol, Austria

[21] Appl. No.: 494,272

[22] Filed: Feb. 23, 1990

Related U.S. Application Data

[63] Continuation of Ser. No. 382,144, Jun. 27, 1989, abandoned, which is a continuation of Ser. No. 211,536, May 5, 1988, abandoned.

[51] Int. Cl.$^5$ .................. C07D 501/46; A61K 31/545
[52] U.S. Cl. .................................................... 540/225
[58] Field of Search .................... 540/225; 514/206

[56]  References Cited

U.S. PATENT DOCUMENTS 4,497,956  2/1985  Looker ................................ 540/225

FOREIGN PATENT DOCUMENTS 0160565  11/1985  European Pat. Off. .
0166580   1/1986  European Pat. Off. .

*Primary Examiner*—Nicholas S. Rizzo
*Attorney, Agent, or Firm*—Gerald D. Sharkin; Robert S. Honor; Thomas O. McGovern

[57]  ABSTRACT

The invention relates to new stable, crystalline forms of the t-butylester of ceftazidime of formula

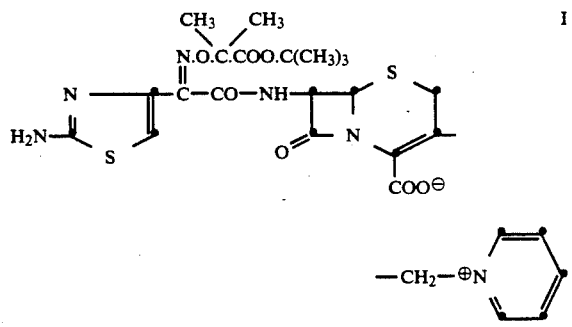

and the production thereof.

3 Claims, No Drawings

STABLE, CRYSTALLINE FORM OF A CEPHALOSPORIN INTERMEDIATE PRODUCT

This is a continuation of application Ser. No. 07/382,144, filed Jun. 27, 1989, now abandoned, which in turn is a continuation of application Ser. No. 07/211,536, filed May 5, 1988, now abandoned.

The invention relates to a new stable, crystalline form of (6R,7R)-7-[[2-(2-amino-4-thiazolyl)-(Z)-2-(1-tert-.butoxycarbonyl-1-methylethoxy)-imino]acetamido]-3-(1-pyridiniummethyl)-3-cephem-4-carboxylate (Ceftazidime-t-butylester) of formula

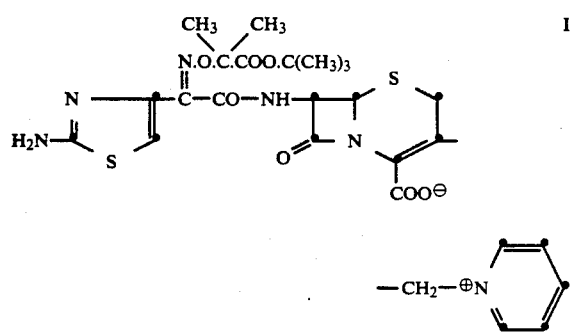

and processes for the production thereof.

The compound of formula I is an important intermediate product in the production of ceftazidime. Ceftazidime is a highly active antibiotic, which has attained exceptional significance following its extensive activity against micro-organisms, especially in the gram-negative range, and is used as a parenteral pharmaceutical, in particular in hospitals, whereby its activity against problem bacteria, such as pseudomonas, is also of importance.

Production of ceftazidimes usually takes place via intermediate stages which contain protecting groups on the amino group of the thiazole ring, on the carboxyl group in the side chain and sometimes also on the carboxyl group of the thiazolidine ring. These protecting groups are split off in one or several reaction steps.

The compound of formula I is notable for these protected ceftazidime intermediate stages, since when they are further processed to ceftazidimes, e.g. by acid hydrolysis, only isobutyl alcohol is obtained as a by-product and the ceftazidime can be isolated in high purity and a good yield. In WO 85/4659, there is described an especially simple method of producing the compound of formula I by reacting the activated thiol ester of formula

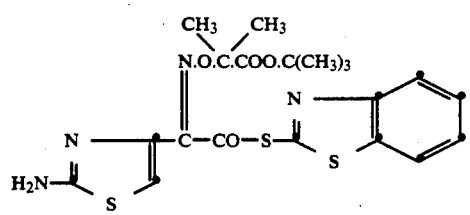

in syn-form with the compound of formula

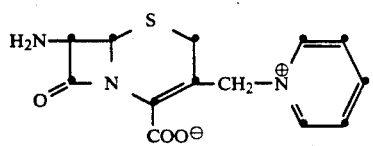

However, using the process given in this application, the compound of formula I is only obtained in amorphous form which is difficult to isolate.

It has now been found that when using suitable solvents, the compound of formula I can be isolated from the reaction mixture in crystalline form, in good yield and purity, by means of simple filtration, whereby the by-products and impurities remain in solution.

Suitable solvents are halogenised, aliphatic hydrocarbons, e.g. dichloromethane or chloroform, lower aliphatic alcohols, e.g. methanol to n-butanol, lower aliphatic carboxylic acid esters, e.g. ethyl acetate or butyl acetate, dimethylformamide or dimethyl sulphoxide and mixtures of these solvents. Mixtures of lower alcohols, dimethylformamide or dimethyl sulphoxide on the one hand and aromatic hydrocarbons, e.g. benzene, toluene, chlorobenzenes, or acetone or acetonitrile on the other hand can also be used as solvents. Preferred solvents are mixtures of dichloromethane, chloroform, butyl acetate, ethyl acetate or toluene on the one hand and methanol or dimethyl sulphoxide on the other hand. The ratios of the mixtures are normally between 20:1 and 1:20, and depend on the solubility of the end product.

The activated thiol ester of formula II is produced in known manner, e.g. by reacting the corresponding acid with bis-(benzothiazol-2-yl)disulphide and triphenylphosphine, whereby the reaction mixture can be used for the reaction with the compound of formula IIIa without isolating the thiol ester. The use of isolated thiol ester however gives better yields and purer products.

The compound of formula IIIa may be used as an inner salt or as the addition salt of an organic or inorganic acid. Solvates of these compounds can also be used. Examples of the forms of the compound of formula IIIa which are used are the dihydrate, monohydrochloride.monohydrate, dihydrochloride.dihydrate, hydriodide.monohydrate and oxalate. When using acid addition salts, a quantity of base (e.g. triethylamine) which is equivalent to the acid must b added at latest prior to filtration of the product.

The compound of formula IIIa can therefore be defined in general as follows:

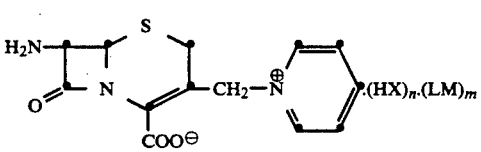

whereby HX signifies an organic or inorganic acid, LM signifies water or an organic solvent and n and m are 0, 1 or 2.

The reaction temperatures are preferably between 0° C. and room temperature. The reaction can however be carried out at lower or higher temperatures, whereby longer reaction times or increased secondary reactions would have to be taken into account.

Filtration of the product is normally carried out at the same temperature as the reaction; to raise the yield or to improve purity of the product, filtration can also be effected at a lower or higher temperature. For the same reasons (yield, purity), the reaction mixture may be diluted prior to filtration with a solvent which has already been used or with an additional solvent, or part of the solvent used can be distilled off.

As already mentioned, the ceftazidime-t-butylester is obtained in crystalline form, in the form of small needles which are doubly refracting under the polarisation microscope. The crystallinity of the product was confirmed by measuring X-ray diffraction of a powder sample:

| d (Å) | I |
| --- | --- |
| 17.0 | w |
| 15.5 | m |
| 5.9 | w |
| 5.0 | w |
| 4.15 | w |
| 3.84 | w |
| 3.3 | w | w = weak
m = medium

This crystalline form is referred to in the following as α-form. This α-form is obtained in high yield in the process according to the invention, but has relatively low stability in storage. For example, if this product is stored for a few days at room temperature ($\sim 25°$ C.), disintegration is observed. This ability to disintegrate (accompanied by the odour of pyridine) is undesirable, and apart from the problems of drying, leads to problems relating to increased expenditure during storage and further processing.

It has now also been found that the compound of formula I can also be obtained in another, more stable form with the highest purity ($\geq 97\%$). This new crystalline modification, called the β-form in the following, can be produced from the amorphous form or also by modifying the isolation of the process for producing the α-form, without or with intermediate isolation of the α-form. The new modification exists as a crystalline powder, which under the polarisation microscope appears as small doubly refracting needles, and whose X-ray spectrum differs characteristically from that of the α-form:

| d (Å) | I |
| --- | --- |
| 22.0 | m |
| 10.0 | w |
| 8.5 | m |
| 7.3 | w |
| 6.7 | m |
| 5.9 | md |
| 5.6 | m |
| 5.3 | wd |
| 4.2 | w |
| 3.94 | w |
| 3.82 | w |
| 3.7 | w |
| 3.3 | w | w: weak
m: medium
d: diffuse

This new β-form of the compound of formula I, corresponding to the present process according to the invention, is recovered from the aqueous phase, whereby the aqueous phase may also contain solvents which can be mixed with water.

The process according to the invention is characterised in that the compound of formula I, which is contained in the reaction mixture in amorphous form or in α-form, is converted into an aqueous phase at a pH value of less than 3, especially pH 1.0 to 2.0, by means of extraction with water or with a mixture of water and a solvent which can be mixed with water, whereby at least 50% water is used, and this aqueous phase can also contain solvents which can be mixed with water. From this aqueous phase, by adjusting the pH value to the range of the isoelectric point of the compound of formula I or thereabouts, that is to the range of 3.5 to 7.5, especially 4.2 to 5.2, the compound of formula I in β-form is brought to crystallisation. The compound of formula I is thus obtained in the form of a highly-crystalline, colourless deposit, which can be easily isolated by filtration. However, the isolated compound in amorphous form or in α-form can also be dissolved in water or in a mixture of water and one or several solvents which can be mixed with water—advantageously in a highly concentrated solution—optionally adding an acid up to about pH 2.0 or thereabouts, then the new crystalline β-form according to the invention can be crystallised out by adjusting the pH value to 3.5–7.5, especially to 4.2–5.2, thus obtaining a colourless crystalline deposit which can be easily isolated and represents the α-form of the compound of formula I according to the invention in a highly pure form ($\geq 98\%$).

If, as described, the procedure starts with the amorphous or resp. the isolated α-form, then it is not absolutely necessary to set the pH value to below 3.0, since the α-form also dissolves well in water or mixtures of water with solvents which can be mixed with water in a neutral range, or resp. at pH values of between 3.5 and 7.5. Indeed, it is also possible than on dissolving the new β-form of the compound of formula I according to the invention already begins to crystallise before all the α-form has gone into solution. This happens in particular when working in highly concentrated solutions (>10%) when using pure water without adding solvents. In principle, it is not necessary for all the α-form to be brought into solution before the new β-form according to the invention precipitates, since even when an intermediately clear solution has not been obtained, the starting material completely dissolves in the existing suspension (already-precipitated new β-form present) and is converted into the new β-form according to the invention.

To further clarify this, especially on a larger scale, and to obtain a stable, clear solution (for possible filtration of foreign bodies or after adding adjuvants such as active charcoal etc. for purification purposes), an effort should be made to produce a clear, resistant solution (without having to expect the new β-form to crystallise out). This may be achieved by adding an acid, whereby it is favourable to use at least 1 equivalent of acid, so that the compound of formula I is kept in solution as an acid adduct (salt). In order to obtain the desired new crystalline β-form according to the invention, the quantity of base which is required to neutralise the previously added acid is then added, whereby the new β-form of the compound of formula I can be crystallised from the aqueous solution and isolated.

The acids which are used both during isolation from the reaction mixture, and for producing the new β-form by means of conversion from the isolated α-form, may be all conventional inorganic and organic acids, in particular sulphuric acid and hydrochloric acid, with hydrochloric acid being especially suitable.

The solvents which can be mixed with water may be alcohols, acetone, acetonitrile and those in which the β-form of the compound of formula I according to the invention does not dissolve or only dissolves poorly. Of the alcohols, ethanol, isopropanol, n-propanol and also n-butanol are therefore suitable, while methanol is only suitable in small concentrations, since in higher concentrations, it increases the solubility of the new β-form of the compound of formula I too greatly. In general, the addition of solvents which can be mixed with water is not necessary, and it is favourable to use only water as the extraction or dissolving and precipitation medium, since the solubility of the new β-form of the compound of formula I according to the invention is thus at its lowest, and thus the highest yields are obtained.

In the following examples, which illustrate the invention more fully, but in no way limit its scope, all temperatures are given in degrees celsius. The specific optical rotation $[\alpha]_D^{20}$ was measured in water/methanol 1:1 at a concentration of 1 g/100 ml.

The identity of the products was checked by NMR: $^1$H-NMR (90 MHz, DMSO-d$_6$/D$_2$O/DCL): 8.1 to 9.1 (5H, pyridinium); 7.15 (1H, s, thiazole); 5.92 (1H, d, J=5 Hz, H$_7$); 5.6 (2H, CH$_2$-N); 5.32 (1H, d, J=5 Hz, H$_6$); 3.6 (2H, S-CH$_2$); 1.55 (6H, s, C(CH$_3$)$_2$); 1.40 (9H, C(CH$_3$)$_3$).

EXAMPLE 1

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form)

12 g of 2-(2-amino-4-thiazolyl)-(Z)-2-[(1-tert.butoxycarbonyl-1-methylethoxy)imino]thioacetic acid-S-benzothiazol-2-yl-ester, 7.7 g of (6R,7R)-7-amino-3-(1-pyridiniummethyl)-3-cephem-4-carboxylic acid.chloride.monohydrate and 3.8 ml of triethylamine are stirred for 10 hours at 0° in a mixture of 75 ml of dichloromethane and 5 ml of methanol. The solid substance is filtered off, washed with dichloromethane and vacuum-dried at room temperature. 10.5 g of the title compound are obtained in the form of a colourless crystal powder (=78% of theory).
Purity: 97%; $[\alpha]_D^{20} = -36.4°$.

EXAMPLE 2

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form)

A preparation as in example 1 is stirred for 4 hours at room temperature in 80 ml of dichloromethane. The reaction suspension is heated to 40° and the solid substance filtered off. 10 g of the title compound are obtained (=75% of theory) in crystalline form.
Purity: 95%; $[\alpha]_D^{20} = -36.2°$.

EXAMPLE 3

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form)

A preparation as in example 1 is stirred for 20 hours at 0° and then for 2 hours at −20° in 50 ml of methanol. The solid substance is isolated as in example 1. 9 g of the title compound are obtained (=67% of theory) in crystalline form.
Purity: 98%; $[\alpha]_D^{20} = -35.6°$.

EXAMPLE 4

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form)

The reaction is carried out as in example 1, but in a mixture of 70 ml of dichloromethane and 10 ml of dimethyl sulphoxide. 8 g of the title compound are obtained (=60% of theory) as crystals.
Purity: 95%; $[\alpha]_D^{20} = -35.8°$.

EXAMPLE 5

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form)

2.4 g of 2-(2-amino-4-thiazolyl)-(Z)-2-[(1-tert.butoxycarbonyl-1-methylethoxy)imino]thioacetic acid-S-benzothiazol-2-yl-ester and 1.3 g of (6R,7R)-7-amino-3-(1-pyridiniummethyl)-3-cephem-4-carboxylate.monohydrate are stirred for 6 hours at 0° in a mixture of 15 ml of dichloromethane and 5 ml of methanol. The solid substance is isolated as in example 1. 1.9 g of the title compound are obtained (=75% of theory) in crystalline form.
Purity: 98%; $[\alpha]_D^{20} = -36.5°$.

EXAMPLE 6

(6R,7R)-7-[[2-(2-amino-4-thiazolyl)-(Z)-2-(tert.butoxycarbonyl-1-methylethoxy)imino]acetamido]-3-(1-pyridiniummethyl)-3-cephem-4-carboxylate (α-form)

19.1 g of 2-(2-amino-4-thiazolyl)-(Z)-2-[(1-tert.butoxycarbonyl-1-methylethoxy)imino]thioacetic acid-S-benzothiazol-2-yl-ester, 14.6 g of (6R,7R)-7-amino-3-(1-pyridiniummethyl)-3-cephem-4-carboxylic acid.iodide.monohydrate and 5.6 ml of triethylamine are stirred for 24 hours at 0° in a mixture of 142.5 ml of dichloromethane and 7.5 ml of methanol. The solid substance is filtered off, washed with dichloromethane and vacuum-dried at room temperature. 16.0 g of the title compound are obtained (=79.6% of theory) in crystalline form.
Purity: 97%; $[\alpha]_D^{20} = -36.7°$.

EXAMPLE 7

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (β-form)

40 g of (6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form) are dissolved in 400 ml of water. This solution is injected with crystals of the β-form whereby a colourless crystalline deposit is formed. After cooling to about +4°, the crystals are isolated, and after washing with water and drying, 27 g of the β-form are obtained.

EXAMPLE 8

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (β-form)

24 g of 2-(2-amino-4-thiazolyl) (Z)-2-[(1-tert.butoxycarbonyl-1-methylethoxy)imino]thioacetic acid-S-benzothiazol-2-yl-ester, 15.4 g of (6R,7R)-7-amino-3-(1-pyridiniummethyl)-3-cephem-4-carboxylic acid.chloride and 7.6 ml of triethylamine are stirred for 20 hours at 0° in a mixture of 150 ml of dichloromethane and 5 ml of methanol. Then, 100 ml of water and 20 ml of conc. HCl are added to the reaction mixture, and the phases are separated. The cold aqueous phase is filtered, and then the pH value of the solution is adjusted to 4.8-5.0 with 3N NaOH, whereby the temperature rises to 20°-22° and the title compound crystallises out. After cooling to about 4° for 2 hours, the crystals are filtered off, washed with a little cold water, and after vacuum-drying, 16 g of the title compound are obtained in β-form.

EXAMPLE 9

(6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (β-form)

70 g of (6R,7R)-7-[[(2-(2-amino-4-thiazolyl)-(Z)-2-(1-tert.butoxycarbonyl-1-methylethoxy)imino]acetamido]-3-(1-pyridiniummethyl)-3-cephem-4-carboxylate (α-form; 85%) are added to a mixture of 25 ml of conc. HCl and 500 ml of ice water. A clear solution of about pH 1.5 is obtained. The pH value is then adjusted to 4.8-5.0 with 2N NaOH, and the temperature thus rises to 18°-22°. The title compound crystallises in the form of a colourless deposit. Cooling is subsequently effected for 2 hours to +4°, and then the crystals are isolated, washed with cold water (100 ml) and the moist cake is dried on a fluidised bed with air of 45°-50°. In this way, 52 g of highly pure (≧98%) title compound of the α-form are obtained with a H₂O content of 8.6%.

We claim:

1. The crystalline, stable form of (6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (ceftazidime-t-butylester) of formula

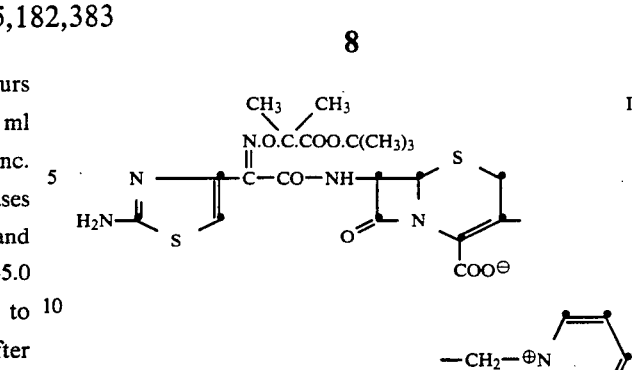

having the X-ray spectrum

| d (Å) | I |
| --- | --- |
| 17.0 | w |
| 15.5 | m |
| 5.9 | w |
| 5.0 | w |
| 4.15 | w |
| 3.84 | w |
| 3.3 | w | w = weak
m = medium (α-form).

2. The crystalline, stable form of (6R,7R)-7-[[2-(2-amino-4-thiazolyl)-(Z)-2-(1-tert.butoxycarbonyl-1-methylethoxy)imino]acetamido]-3-(1-pyridiniummethyl)-3-cephem-4-carboxylate (ceftazidime-t-butylester) of formula I, having the X-ray spectrum

| d (Å) | I |
| --- | --- |
| 22.0 | m |
| 10.0 | w |
| 8.5 | m |
| 7.3 | w |
| 6.7 | m |
| 5.9 | md |
| 5.6 | m |
| 5.3 | wd |
| 4.2 | w |
| 3.94 | w |
| 3.82 | w |
| 3.7 | w |
| 3.3 | w | w: weak
m: medium
d: diffuse (β-form).

3. The ceftazadime-t-butyl ester of claim 2 having a purity of at least 97%.

* * * * *